United States Patent
Liu

(10) Patent No.: US 6,767,734 B2
(45) Date of Patent: Jul. 27, 2004

(54) METHOD AND APPARATUS FOR PRODUCING AGE-SYNCHRONIZED CELLS

(75) Inventor: Shi V. Liu, Goshen, NY (US)

(73) Assignee: Shi Liu, Apex, NJ (US)

( * ) Notice: Subject to any disclaimer, the term of this patent is extended or adjusted under 35 U.S.C. 154(b) by 334 days.

(21) Appl. No.: 10/082,906

(22) Filed: Feb. 25, 2002

(65) Prior Publication Data

US 2002/0081727 A1 Jun. 27, 2002

Related U.S. Application Data

(62) Division of application No. 09/605,958, filed on Jun. 28, 2000, now abandoned.

(51) Int. Cl.$^7$ .............................................. C12M 1/00
(52) U.S. Cl. ............................. 435/293.1; 435/299.1; 73/863.83; 73/864.33; 73/864.34
(58) Field of Search ........................ 73/863.83, 864.33, 73/864.34; 435/289.1, 293.1, 299.1

(56) References Cited

U.S. PATENT DOCUMENTS

| | | | | |
|---|---|---|---|---|
| H831 H | * | 10/1990 | Salanitro et al. ............... | 435/34 |
| 5,442,967 A | * | 8/1995 | McClane .................. | 73/863.22 |
| 5,605,836 A | * | 2/1997 | Chen et al. ............... | 435/305.4 |
| 5,817,509 A | * | 10/1998 | Stevens et al. ........... | 435/297.5 |
| 5,989,924 A | * | 11/1999 | Root et al. .................. | 436/518 |

OTHER PUBLICATIONS

Zeuthen, E., Synchrony in Cell Division and Growth, 1964, pp 1–8, Interscience Publishers, New York, USA.
Helmstetter, C.E., Methods for studying the microbial division cycle, Meth.Microbiol 1=327–363, 1969.
Krek, W. and DeCaprio, J.A., Cell synchronization, Meth. Enzymol., 254:114–124, 1995.
Helmstetter, C.E. and Cummings, D.J., Bacterial synchronization by Selection of cells at division, Proc. Nat. Acad. Sci. USA 50 767–774, 1963.
Helmstetter, C.E., Description of a baby machine for *Saccharomyces cerevisae*, New Biologist 3=1089–1096, 1991.
Helmstetter, C.E., et al., Improved bacterial baby machineʋApplication to *Escherichia coli* K–12, J. Bacteriol 174ʋ3445–3449, 1992.
Degnen, S.T. and Newton, A., Chromosome replication during development in *Vanlobater crescentus*, J. Mol. Biol. 64=671–680, 1972.
Egilmez, N.K. et al., Preparation and partial characterization of Old yeast cells, of S. cerevisae, Cell 84ʋ633–642, 1996.
Smeal, T. et al., Loss of transcriptional silencing causes sterility in old mother cells of S cerevisiae, Cell 84ʋ633–642, 1996.
Neidhart, F.C. et al., Physiology of the Bacterial CellʋA Molecular Approach, p 389, Sunder Associates, Inc. Sunderland, MA 1990.
Alberts, B. et al., Molecular Biology of the Cell (2nd Ed.) 1989 p 727 Garland Publishing, Inc. New York (Updated in 3rd Ed in 1994).
Liu, S.V., Tracking bacterial growthin liquid media and a new bacteriol life model, Sciecne in China (Series C) 42ʋ654–654, 1999.
Liu, S.V., What is bacterial life? Logical Biology 2000ʋ5–16,2000, http://www.logibie.com.

* cited by examiner

Primary Examiner—David A. Redding

(57) ABSTRACT

The present invention relates to a method and an apparatus for producing cell population of the same chronological age. Cells of a predetermined age are collected onto an array of surfaces. The collected cells are retained on the said surface during their continuous cultivation and kept from mixing with their descendants by means of flushing away their offspring. Sampling of surface from the array at desired time gives cell populations of desired cell age for examination, assay and other different uses.

16 Claims, 2 Drawing Sheets

METHOD AND APPARATUS FOR PRODUCING AGE-SYNCHRONIZED CELLS

This is a division of application of Ser. No. 09/605,958, filed Jun. 28, 2000 now abandoned.

BACKGROUND OF THE INVENTION

1. Field of the Invention

The present invention relates to a method and apparatus that facilitates the collection of age-homogenous cell population and the maintenance of age synchrony in the collected cell population. More particularly, the invention is directed to a process and equipment for producing truly age-homogeneous cell population by obtaining an initial cell population in a very short period of time and maintaining the age homogeneity of this population during the subsequent aging process by constant removal of their offspring.

2. Description of Related Art (1) The existing methods for cell synchronization.

Since early 1950s, various efforts have been made for obtaining "synchronized" cell population. For comprehensive reviews, see examples by E. Zeuthen (Synchrony in Cell Division and Growth, Interscience Publishers, New York, 1964), C. E. Helmstetter (Meth. Enzymol., 1, 327–363, 1969), and W. Krek and J. A. DeCaprio (Meth. Enzymol., 254, 114–124, 1995). In general, methods developed for cell synchronization can be classified as selection synchronization and induction synchronization.

In selection synchronization, a difference in the physico-chemical properties of the cells in different divisional stages is often used as a basis for "cell cycle" (reproduction cycle) stage-specific separation. The physicochemical properties being utilized can be intrinsic cell properties such as the cell size and the cell density or artificially afforded properties such as the labeled molecules incorporated into the biomass or labeled molecules attached to the cell surface.

In induction synchronization, cells at different developmental stages are stopped at or induced into a predetermined developmental stage. Upon a desired time, these cells are allowed to proceed into subsequent development at the same release time to start the synchronization. The most frequently used agents for stopping or inducing cell development are those that interfere or promote "cell cycle" (cell reproduction cycle).

A special cell synchronization device called "baby machine" has been developed (C. E. Helmstetter and D. J. Cummings, Proc. Natl. Acad. Sci. USA, 50, 767–774, 1963; C. E. Helmstetter, New Biol., 3, 1089–1096, 1991; C. E. Helmstetter et al., J. Bacteriol., 174, 3445–3449, 1992). With this approach, baby cells released from the cells bound to a filter are collected and are allowed to grow together in further cultivation. It is hoped that the continuous cultivation of these baby cells should yield cell cycle synchrony for long time. But in reality, this expectation has never been realized, even when this method is used for synchronization of *Escherichia coli* and yeast (C. E. Helmstetter, New Biol., 3, 1089–1096, 1991; C. E. Helmstetter et al., J. Bacteriol., 174, 3445–3449, 1992).

A plate release technique has been used for synchronizing Caulobacter, an asymmetric bacterium that divides into a swarmer cell and a stalked cell (S. T. Degnen and A. Newton, J. Mol. Biol. 64, 671–680, 1972). Due to the adhesive property of the holdfast at the tip of the stalk, stalked cells attach to the surface such as the plate surface of the Petri dish and remain attached during their subsequent cell divisions. However, swarmer cells swim into the liquid phase once there are divided from the attached stalked cells because the motor activity of the polar flagellum on each swarmer cells. Thus, cell age synchronization of Caulobacter can be started simply by collecting swarmer cells released in a short period when they are divided from the adhered stalked cells. However, many studies have repeatedly shown that subsequent cultivation of these age-synchronous swarmer cells unavoidably leads to cell cycle asynchrony once the second cell cycle starts. This is because, while a stalked cell will divide soon after it finish the first cell cycle, a swarmer cell must grow into a stalked cell and then enters the next cell cycle. Thus, to achieve continuous cell cycle synchronization of Caulobacter, it is necessary to perform repeated density centrifugation to separate the two types of Caulobacter cells. This repeated centrifugation process is labor-intensive and time-consuming. For this reason, few studies on Caulobacter have extended into the second cell cycle of its life span.

Some methods have been developed for obtaining old cells of budding yeasts. One method is based on the size/density difference between the bigger mother cells and the smaller baby buds and requires successive repetition of rate-zonal sedimentation in sucrose density gradients to separate larger old cells from smaller young cells (N. K. Egilmez et al., J. Gerontol. Biol. Sci., 45, B9–B17, 1990). Another method depends on selectively labeling young cells with biotin and then obtains these biotin-labeled cells when they grow older through the binding between biotin and avidin, which is coated on magnetic beads (T. J. Smeal et al., Cell, 84, 633–642, 1996).

(2) The drawbacks of existing methods for cell synchronization.

It is well known that all existing methods of cell synchronization are inadequate for maintaining cell division synchrony for more than a few cell division cycles, whether the cells populations are prokaryotic unicellular microorganisms, eukaryotic unicellular microorganisms, or eukaryotic tissue cells of multicellular organisms (E. Zeuthen, Synchrony in Cell Division and Growth, Interscience Publishers, New York, 1964; C. E. Helmstetter et al., J. Bacteriol., 174, 3445–3449, 1992). The underlying causes for such rapid deterioration of the synchrony in continuous culture of the initially synchronized cell population remains enigmatic.

A fundamental assumption made explicitly or inexplicitly for existing cell synchronization methods is that two cells formed from one cell are daughter cells of the same generation and of the same age (F. C. Neidhardt et al., Physiology of the Bacterial Cell: A Molecular Approach, Sinauer Associates, Inc., Sunderland, Mass., 1990; B. Alberts et al., Molecular Biology of the Cell, 3rd ed., Garland Publishing, Inc., New York, 1994). Because of this widely held but unproven assumption, it is generally believed that, once a cell population is obtained at or induced to the same cell division stage, it should automatically yield cells of the same division stage (often inappropriately called the cell age) during the subsequent cultivation.

However, this dogmatic view of cell life and cell synchronization is contradictory to the reality of many forms of cellular life and is also logically fallacious (S. V. Liu, Logical Biology, 2000, 5–16, 2000). A new model for cellular life proposes that the two cells formed from the division of one cell really belong to two successive generations and of different ages (S. V. Liu, Science in China, 42, 644–654, 1999). If the new model is correct, it means that the fundamental assumption made in most existing cell synchronization methods is invalid.

Collectively, the existing methods for cell synchronization often suffer one or more of the following drawbacks:

(a) The initial cell population used for starting cell synchronization often comprises cells of different ages. It has been widely believed that cells at the same divisional (reproduction) stages are of the same age. However, this assumption does not reflect all the reality and is logically invalid. For example, to say that all pre-divisional cells are of the same cell age is just like to say that all the pre-laboring mothers are of the same age. This statement is not true because even women of different ages can become pregnant at the same time and thus become "synchronous" in their reproduction stages.

(b) Cells belong to different generations are mixed in the continuous cultivation of the initially cell divisional stage- or cell age-synchronized cell population. The basic assumption of one mother cell divides into two daughter cells violates the fundamental principle of biological reproduction, which means a process for generation succession and genetic inheritance. Although final disproval of this erroneous assumption requires further scientific investigations, it is not difficult to point out the logical flaw of this argument and its incompatibility with the general principle of life. For example, no one would believe that a female human being would become just one of her offspring after she finishes the laboring. Thus, without separating the offspring from their parents, the continuous cultivation of the initial age-synchronous cell population will naturally lead to a mixing of two successive generations and thus age heterogeneity. To illustrate this point with a more familiar form of live—the human being, no one would believe that a human population consisting of the same age of different females will remain its age homogeneity if their newborns stays together with them.

(c) Induction synchronization methods developed today are capable of achieving only the cell division (reproduction) synchronization, not necessarily the cell age synchronization. Theoretically, all agents affecting the cell cycle (cell reproduction cycle) works on all cells regardless of their ages. It is thus possible to make cells of different chronological age to be stopped at or to be induced into the same reproductive (cell cycle) stage. For this reason, cell cycle-synchronized cell population is not necessarily cell age-synchronized.

(d) Tedious and unnatural procedures are used in age-specific cell synchronization methods. So far only a few methods can be used to obtain truly age-homogenous cell populations at the age older than one cell reproduction cycle and these methods are used for obtaining old yeast cells (N. K. Egilmez et al., J. Gerontol. Biol. Sci., 45, B9–B17, 1990; T. J. Smeal et al., Cell, 84, 633–642, 1996). However, these methods require tedious processes and specialized agents or equipments. For example, repetitive centrifugations are required for collecting old yeast cells and separating them from young budding cells in order to achieve long-term cultivation of the initial mother cells. This repeated centrifugation is cumbersome, time-consuming, and labor-intensive. Besides, cells treated by this process also experience unnatural physiological conditions. Another technique developed for obtaining age-specific population of yeasts involves labeling baby yeast cells with biotin and then retrieving these biotin-labeled cells at their older ages by using magnetic beads coated with avidin which specifically bind biotin (T. J. Smeal et al., Cell, 84, 633–642, 1996). This method involves artificially change cell properties and can be used only for those cells that can incorporate biotin onto their cell surface. The method also requires a special instrument—a magnetic sorter.

Another technique that holds a promise for obtaining cells of the specific age is flow cytometry, if cells can be labeled at specific age and such labeling molecules can be tracked by the flow cytometry. However, if the collection process spreads over a long period of time, then a chronological age gap will still exist among the different cells. Thus, flow cytometry maybe inadequate and certainly is expensive for obtaining large number of age-synchronized cell population.

In essence, all existing "one-step" synchronization methods, which desire to achieve long-term cell synchronization by just obtaining the initial cell population of the same division cycle stage or cell age, are theoretically unable to produce truly age-synchronized cell population in subsequent cultivation of the population. Those "multiple-step" synchronization methods, which required repeated centrifugal separations or requires first labeling the cells and then retrieving the labeled cells, can obtain truly age-homogenous cell population at the old ages but takes a lot of time, cost, and labor. Cells obtained through these methods often experience unnatural living conditions and these artificial stresses may interfere with the study of the physiological status of the cells.

BRIEF SUMMARY OF THE INVENTION

OBJECTS OF THE INVENTION

There is no prior synchronization method that satisfies the two essential requirements for obtaining truly age-synchronized cell population: the collection of initial cell population at a very narrow range of specific cell age and the continuous cultivation of the initial cell population in a manner that avoids them being mixed with their offspring. Besides, in all existing methods for cell synchronization, the processes for producing synchronized cell population and processes for monitoring cell development/verifying cell synchronization status are separate tasks. This adds difficulty for real-time control of the cell synchronization process.

It is therefore a primary object of the present invention to develop a means for easily obtaining truly age homogenous cell population for long period of cultivation.

It is also an object of this invention to find a means for obtaining cell synchrony in a most natural and least stressful way.

It is another object of the present invention to find a method that can be used simultaneously for monitoring the development and synchrony of the cell population and for obtaining the synchronous cell population.

It is still another object of this invention to provide a scalable method of cell synchronization that can be adjusted to the different requirements.

It is also an objective of this invention to design a cell synchronization process that can be easily automated.

ADVANTAGES OF THE INVENTION

The present invention pertains to a generalized method and apparatus that can result in long-term age synchronization of cell population. It is based on a newly proposed theory of cell life that claims a parent-child relationship between the two cells formed from one cell. From this new understanding of cell life, it is understood that true age synchronization of any cell population can be achieved only through the absolute separation of the original parent cells from any of their offspring cells.

The present invention differs from all previous cell synchronization methods. First, an initial cell population is captured onto the surface within a very short period of time to ensure the highest age homogeneity in the initial cell population. Second, only the initially captured age-homogeneous cells are kept and their offspring are continuously removed so that the age purity of the initial population is maintained. Third, when using a transparent surface material to capture the initial cell population, the status of cell synchronization can be continuously monitored, either by installing a microscopic lens directly above one area of the cell-attached surface or by taking a piece of the surface for microscopic examination. This in-process monitoring allows collection of cells at the desired specific cell age and cell reproduction stage. Fourth, the initial cell populations can be captured on individual surface areas that are separately mounted. This allows multiple collections of cells at the different cell ages without disrupting the operation of overall process.

In comparing with the baby machine, the present invention obtains highly age-homogenous initial cell population and continuously maintains the age purity in the subsequent cultivation. In the baby machine, cells immobilized onto a surface come from an exponential-phase culture, which in fact contains cells of various ages, as indicated by the wide size distribution. Thus, without an age-differentiating measure, cells of any age can adhere to the surface. Besides, the contact time allowed for cells to adhere to the surface is too long relative to its length of cell reproduction cycle. This long duration of collecting initial cell population introduces a great age difference among the collected cells. The consequence of these shortcomings is that cells collected on the same surface do not divide in a synchronized fashion. When cell synchronization begins with an age-mixed population, long-term cell age synchronization will be difficult, if not impossible, to achieve. The present invention overcomes these shortcomings by obtaining only the newborn cells in a very short period of time. This will insure a high age synchrony in the initial cell population and. Furthermore, although baby machine can collect baby cells as the starting population for synchronization, it does not separate the offspring from the parent in the continuous cultivation of this initial population. Thus, age mixing occurs in all subsequent cultivation of the culture. The present invention overcomes this problem by constantly removing the offspring from the initially captured cells.

In comparing with the methods developed for obtaining old yeast cells, the present invention employs more natural and simpler procedures. The invention takes advantage of the adhering capability of some microorganisms and thus does not introduce any foreign substance or force in collecting these microorganisms. Alternatively, the methods may use a surface that has been made attractive to the cells that lack natural adhering capacity. Compared with the repeated centrifugations employed in the some methods for achieving long-term synchrony, the present invention represents a natural way of achieving cell synchronization.

Other advantages of the present invention include:
(a) low cost for equipments and reagents;
(b) high speed in obtaining synchronized cells;
(c) great flexibility for satisfying the different demand;
(d) convenience for on-line real-time monitoring of the synchronization process;
(e) opportunity for obtaining cells of different ages;
(f) feasibility for automation.

BRIEF DESCRIPTION OF THE DRAWING

Drawing Figures

DETAILED DESCRIPTION OF THE INVENTION

General Procedures

Figure 1:
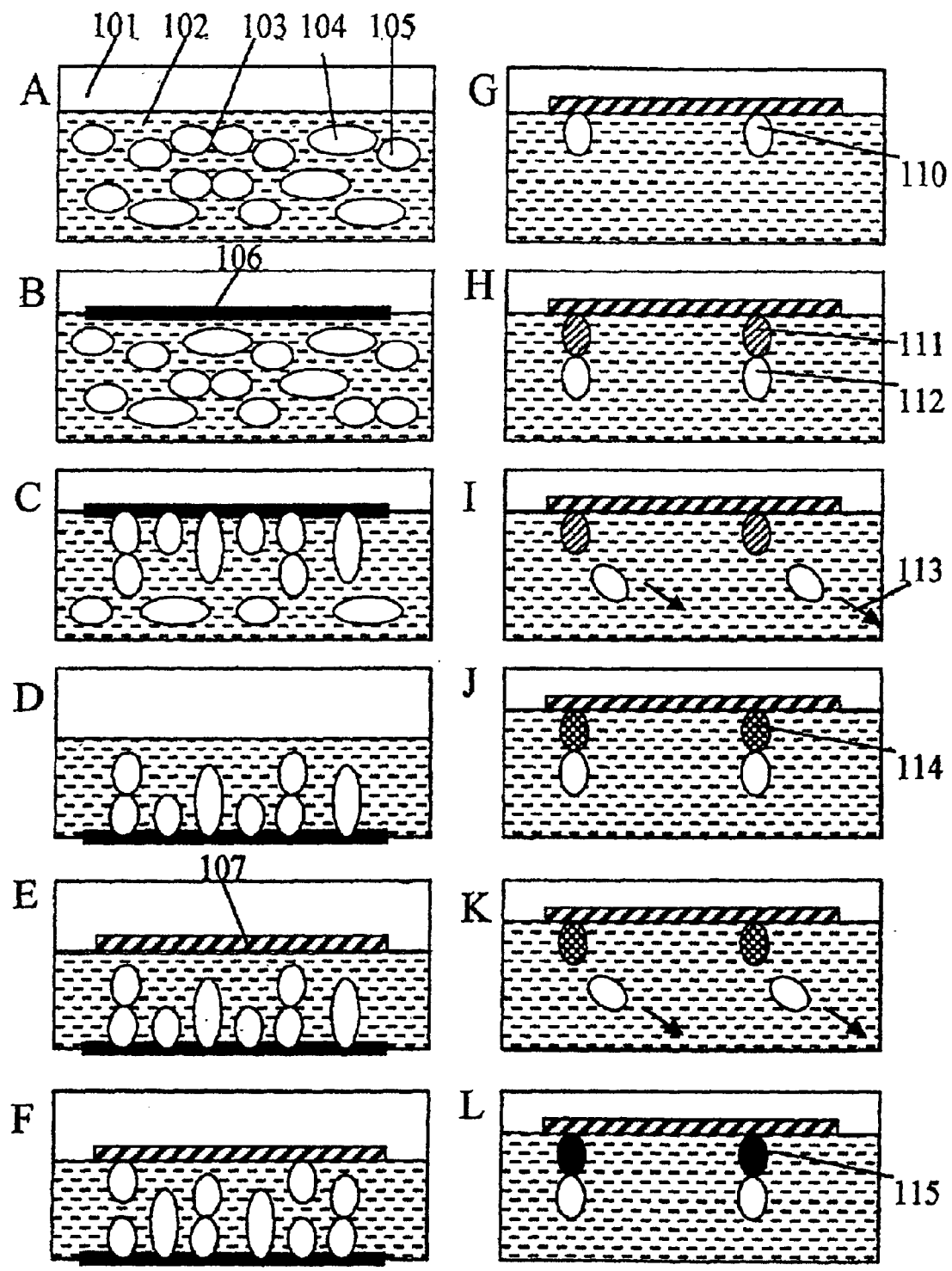
FIG. 1 shows a schematic process of capturing age-homogenous cells and maintaining age purity of these captured cells in their continued cultivation.

The fundamental difference between present invention and previous methods of cell synchronization is that present invention emphasizes not only the necessity of ensuring age purity of the initially collected cell population but also the necessity for maintaining this age purity during the subsequent cultivation.

The collection of age-homogenous initial cell population may be achieved by different ways. In one preferred method, a large number of asynchronous cells are allowed to adhere to a surface. The cell-attached surface should be washed several times to remove any loosely attached cells and then placed into another vessel containing fresh medium, with the adhered cells on the upper side. The firmly attached cells are allowed to grow. Shortly prior to their expected time of reproduction, another new surface is placed close to but not in direct contact with the adhered cells. The new surface is placed there for a very short period of time so that the cells collected onto this new surface have minimal age variation.

Alternatively, various agents can be used to either stop cell development at a specific stage or to induce cell development into a specific stage. Then these cells of the same developmental stages are allowed to reproduce and the newborn cells are collected onto a new surface in a very short period of time.

Still another method for collecting age-homogenous cell population involves labeling cells at a specific age and then collecting these labeled cells by means of binding only the labeled cells. Preferably, the label should be incorporated only into the newborn cells so that the cells can be collected at or immediately after their birth. For example, biotin can be used to label newborn cells and these newborn cells can be easily separated from cells of any other age through the specific interaction between biotin and avidin, which is coated on the surface of magnetic particles.

The maintenance of cell age purity of the collected cells during their subsequent cultivation can be achieved through different ways of removing their offspring in subsequent reproductions. In one preferred method, a horizontal flow of liquid current can be used to carry away the newborns detached from their mother cells. Continuously injecting fresh medium into the incubation chamber and removing old medium will create a current that will take away the detached cells.

Alternatively, the surface containing the adhered cell may be intermittently raised above the liquid medium and then submerged into the liquid medium to create a disturbance that may help the detachment of the offspring. The liquid medium is completely replaced once a while to avoid or, at least, greatly reduce the attachment of offspring to the surface containing the initially collected cells.

To reduce the cost of the above operations, used medium may be filtered to remove cells that may be contained. This cell-free and reconditioned medium may be used again.

Surface materials to be used in the invention include any substance to which an interested type of cell attaches with sufficient strength to be retained during extended period of continuous cultivation. Such surface materials include but are not limited to plastic and glass surfaces. The surface may be untreated or treated with other materials that can enhance the attraction for the cells and the adherence of the cells. Such surface treating material include but not limited to compounds such as poly-L-lysine.

To illustrate how the present invention achieves cell age-synchronization, FIG. 1 presents a schematic diagram of the overall process. An incubation chamber 101 is filled with a liquid medium 102 in which asynchronous cells of various ages exist. The differences in the cell age among these cells are undetermined but can be reflected by the differences in their sizes and morphologies such as a predivisional cell 103, an elongated growing cell 104 and a newborn small cell 105.

To collect cells that will be used as the mother cells for future synchronization, a surface plate 106 is floated on top of the liquid culture. Cells of various ages and in various reproduction stages may be collected onto the surface either due to their intrinsic adhering capacity or due to the passive attraction onto the specially treated surface. The cells collected on the surface are washed with fresh medium to remove any loosely attached cells. Then the whole surface is placed into a new medium, with the cells staying on the upper side of the surface.

To collect newborn cells reproduced from the adhered mother cells, a new surface plate 107 is placed in close distance to the attached cells. The new surface is allowed to stay for a very short time so that all collected newborn cells have only a minimal age difference, as represented by the uniform cell size and shape 110. Then the surface plate containing these newborn cells is placed into a new medium in a different container to start the cell-age synchronization.

During the subsequent cultivation, the newborn cells grow old and into reproductive cell 111 that will give birth offspring 112. To maintain the age purity of the initially collected cells, it is necessary to prevent newborn cells from attaching to the surface. To achieve this, a liquid current 113 may be used to wash off the detached offspring.

With extended cultivation, the initially collected cells will continuously age, as indicated by increasing shading in the drawing of these cells from the hatched pattern 111, to the crossed pattern 114, and to the solid black pattern 115. However, the age purity within this initially collected cell population remains high, due to the constant removal of their offspring.

Cell-aging Machine (CAM)

Figure 2:
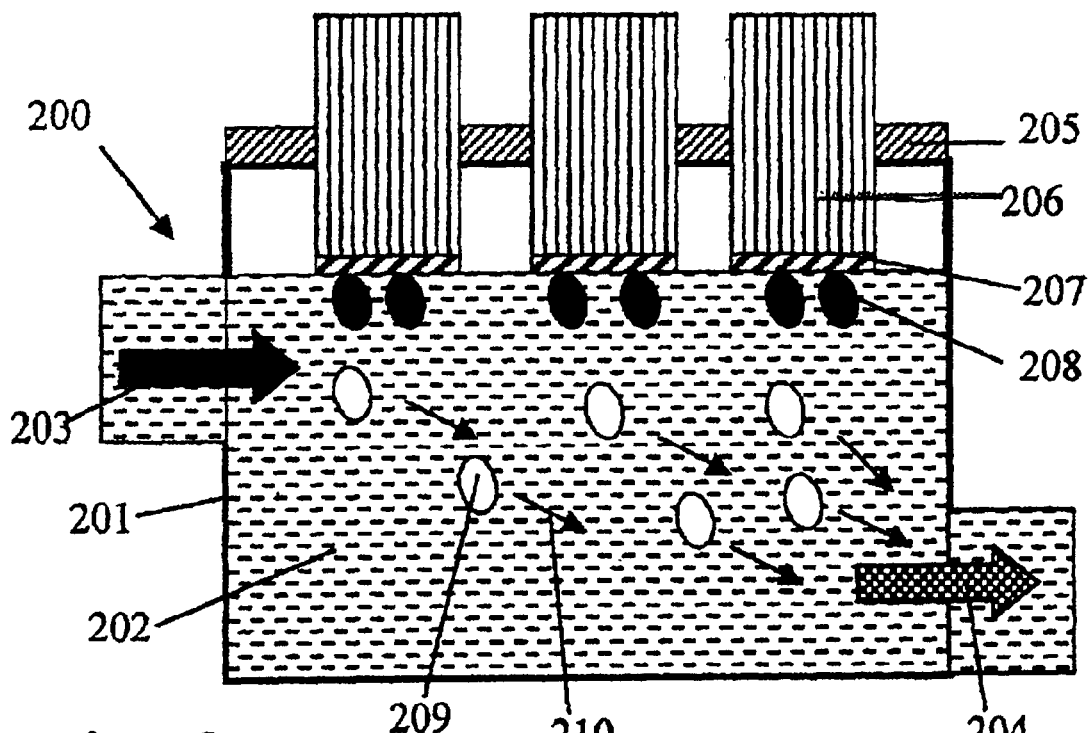
FIG. 2 shows essential components of a cell-aging machine (CAM).

Ideally, the above procedure should be automated and be conveniently accomplished with the use of one single instrument. For this purpose, a special apparatus named cell-aging machine (CAM) is invented. A typical embodiment of CAM is shown in FIG. 2, which only schematically represents the essential parts of the machine for the illustrative purpose and should not be interpreted in any limiting sense.

The apparatus 200 comprises a container 201 for holding liquid medium 202. A flat plate 205 is used as a cover for the upper opening of the container and serves as a holder for a pleural of poles 206 that are individually inserted into the plate. At the bottom of the pole, a surface disk 207 is attached. This surface is used for collecting the initial cell age-homogeneous cell population 208. The cell age purity of this initially collected cell population is maintained by constantly injecting cell-free medium in the inlet 203 to create a horizontal current 210 to carry away offspring cells 209 into the outlet 204.

Figure 3:
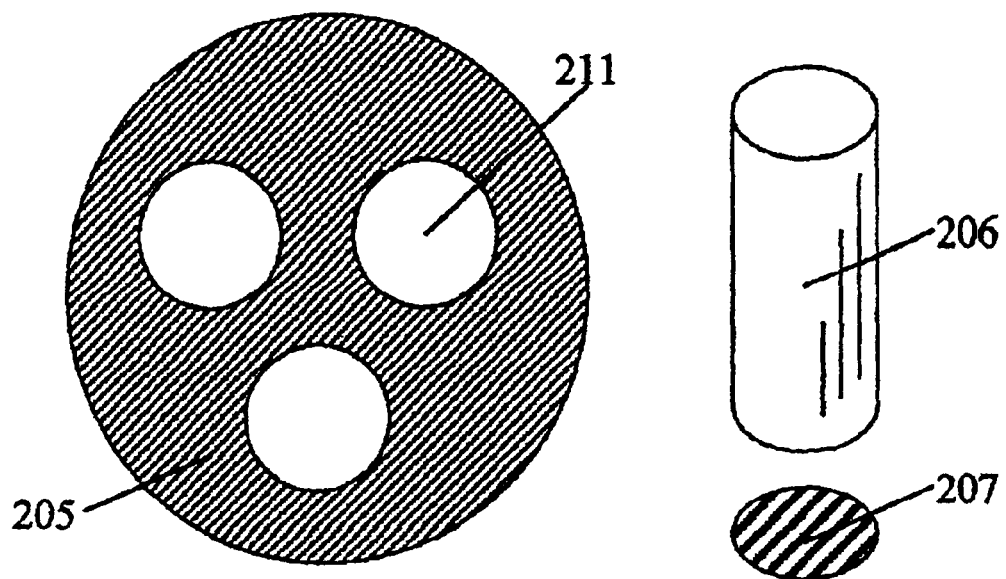
FIG. 3 shows a basic design for the surface array.

FIG. 3 shows one preferred embodiment of the holding plate and the matching retrievable pole and surface disk that collectively constitutes a surface array. The circular solid plate contains a number of holes 211 into which the poles 206 can be inserted. The flat circular surface disk 207 attaches to the bottom end of the pole.

The multiple surfaces in the array-like design allow multiple independent samplings over the cultivation time without interrupt the overall cultivation. The design also allows easy adjustment of the number of surface to be used and the size of each surface. For example, small surface disk may be used for monitoring the progress of the cell aging and cell reproduction, while large surface disks are reserved for obtaining a large number cells for biochemical testing.

A pump may be used for maintaining the current flow of the liquid medium through the incubation chamber. The used medium may be filtered in-line or off-line and the cell-free medium may be circulated back to the chamber.

The surface array may be mounted onto a mechanic device that can intermittently raise and submerge the surface array so that the surface disks contact the liquid medium transiently and the offspring cells have less chance to attach to the surface.

In addition, the growth and reproduction of the cells captured on the surface may be monitored on-line by charge-coupled device (CCD) imaging and video-microscopy or off-line by conventional microscopy.

Summary, Ramifications, and Scope

From the above description of the general procedures and the preferred embodiments of the apparatus, it is clear that the present invention differs from all prior art and produces genuine age synchronization of cell population. The whole process is natural and simple. The operation can be easily automated and fully scalable. The invention provides opportunity for on-line and real-time monitoring of the synchronization process. The collection of cells can be made at the precise cell age and cell reproduction cycle stage. The collected cells are ready for immediate use without further treatment.

The present invention finds utility in various processes related with cell aging and cell reproduction, for example, the senescence of unicellular microorganisms and isolated tissue cells of multicellular organisms and the reproduction control in normal and malignant cells. Such knowledge on cellular aging and cell reproduction is fundamental to the understanding of aging and reproduction in more complex life forms and the biology of cancer and apoptosis. In comparison with prior scientific knowledge and art techniques, the new method and apparatus captures and maintains truly age-homogenous cell population and thus allows straighfforward and reliable examination and testing of living phenomena related to cell aging and cell reproduction.

Besides collecting age-synchronized cells, the ramifications of the present invention include using this invention for efficiently collecting cell age-specific biological products, studying the effect of various agents on the cells at the different ages and reproductive stages, and observing natural temporal profile of gene expression during the cell aging and cell reproducing processes.

It should be pointed out that cells suitable for use in accordance with the present invention include but not limited to the unicellular organisms such as bacteria and yeasts.

It is possible to use this invention to synchronize tissue cells of multicellular organisms. Thus, the scope of the invention should be determined by the appended claims and their legal equivalents, rather than by the examples given.

I claim:

1. An apparatus for constant removal of offspring cells reproduced from retained cells and instant retrieval of retained cells during their growth and aging process, comprising:
   (a) a cover comprising a flat plate having multiple holes and a plurality of poles individually inserted into said multiple holes to provide for immobilizing cells;
   (b) a container matching said cover in size and shape and having at least one inlet and at least one outlet on the opposite sidewall of said container;
   (c) a connection means combining said cover with said container to form a closed chamber; and
   (d) a fluid circulation means connected with said container for driving a horizontal liquid current through said container.

2. The apparatus of claim 1, wherein said flat plate of said cover has a shape including round, rectangle, and polygon.

3. The apparatus of claim 1, wherein said multiple holes on said flat plate of said cover has a shape including round, rectangle, and polygon.

4. The apparatus of claim 1, wherein said plurality of poles is made of materials including glass, plastics, metal, and rubber.

5. The apparatus of claim 1, wherein said plurality of poles matches in size and shape to the size and shape of respective said multiple holes that they are inserted.

6. The apparatus of claim 1, wherein said plurality of poles extend below the bottom surface of said flat plate when they are inserted into said multiple holes on said flat plate.

7. The apparatus of claim 1, wherein the bottom of said plurality of poles is coated with a substance including poly-L-lysine, avidin, and antibody.

8. The apparatus of claim 1, wherein the bottom of said plurality of poles is covered with one or more objects comprising a sheet of plastic film, a piece of filter membrane, a plastic disc, and a glass disc.

9. The apparatus of claim 8, wherein the exposed surface of said objects covering the bottom of said pole is coated with a substance including poly-L-lysine, avidin, and antibody.

10. The apparatus of claim 1, wherein said connection means combining said cover with said container to form a closed chamber includes engaging the outer rim of said cover with the top of the sidewall of said container by a pair of matching ridge and grove respectively constructed on the cover and container and holding the cover and the container together by a clamp.

11. The apparatus of claim 1, wherein said liquid includes plain water and water amended with nutrient components.

12. The apparatus of claim 1, wherein said fluid circulation means includes injecting liquid into said inlet and withdrawing liquid from said outlet on said container.

13. The apparatus of claim 12, wherein said action of injecting and withdrawing liquid is achieved through using a pump.

14. The apparatus of claim 13, wherein the operation of said pump is controlled by a computer.

15. The apparatus of claim 1, further including a device for maintaining the temperature of said liquid at a predetermined value.

16. The apparatus of claim 15, wherein said device for maintaining the temperature comprises a heating unit, a cooling unit, and a regulation unit.

* * * * *